United States Patent [19]

Wilson

[11] Patent Number: 4,676,954

[45] Date of Patent: Jun. 30, 1987

[54] AIR FRESHENER

[76] Inventor: James L. Wilson, 218 Allison Ave., Houston, Pa. 15342

[21] Appl. No.: 861,822

[22] Filed: May 12, 1986

[51] Int. Cl.⁴ .......................... A61L 9/12; F24F 3/12
[52] U.S. Cl. .................................... 422/124; 126/113
[58] Field of Search .................. 98/105, 109; 126/113; 422/123, 124, 125

[56] References Cited

U.S. PATENT DOCUMENTS

| | | | |
|---|---|---|---|
| 3,136,829 | 6/1964 | Skerritt | 126/113 X |
| 3,209,744 | 10/1965 | Ayres et al. | 126/113 |
| 3,355,155 | 11/1967 | Heltzen et al. | 126/113 X |
| 3,366,775 | 1/1968 | Mycue | 422/125 X |
| 3,491,746 | 1/1970 | Swimmer et al. | 126/113 |
| 3,930,797 | 1/1976 | Gertz | 422/124 |
| 4,067,692 | 1/1978 | Farris | 422/124 |

Primary Examiner—Harold Joyce
Attorney, Agent, or Firm—William J. Ruano

[57] ABSTRACT

A forced air furnace air freshener attached to a cold air return duct thereof. A pair of vertically spaced openings are provided in a wall of the duct. A basket has its lid mounted on the outside of such wall, which lid carries a scent block. The hinged main portion of the gasket is normally closed so that air flowing through the cold air duct is by-passed through said openings and is scented by said scent block.

2 Claims, 3 Drawing Figures

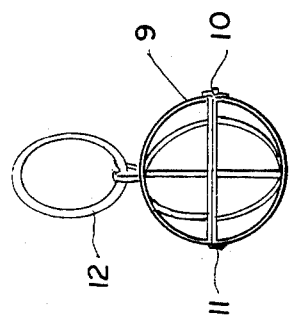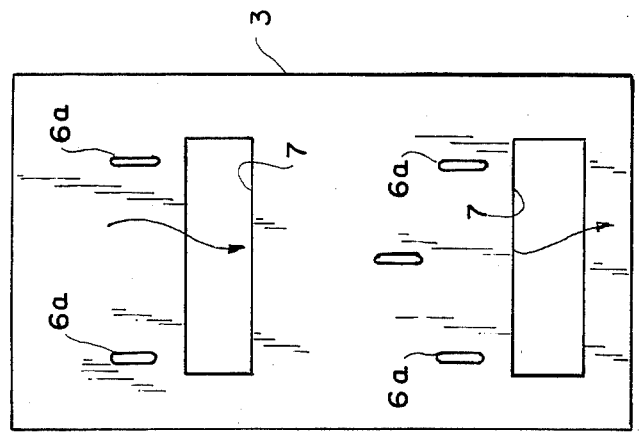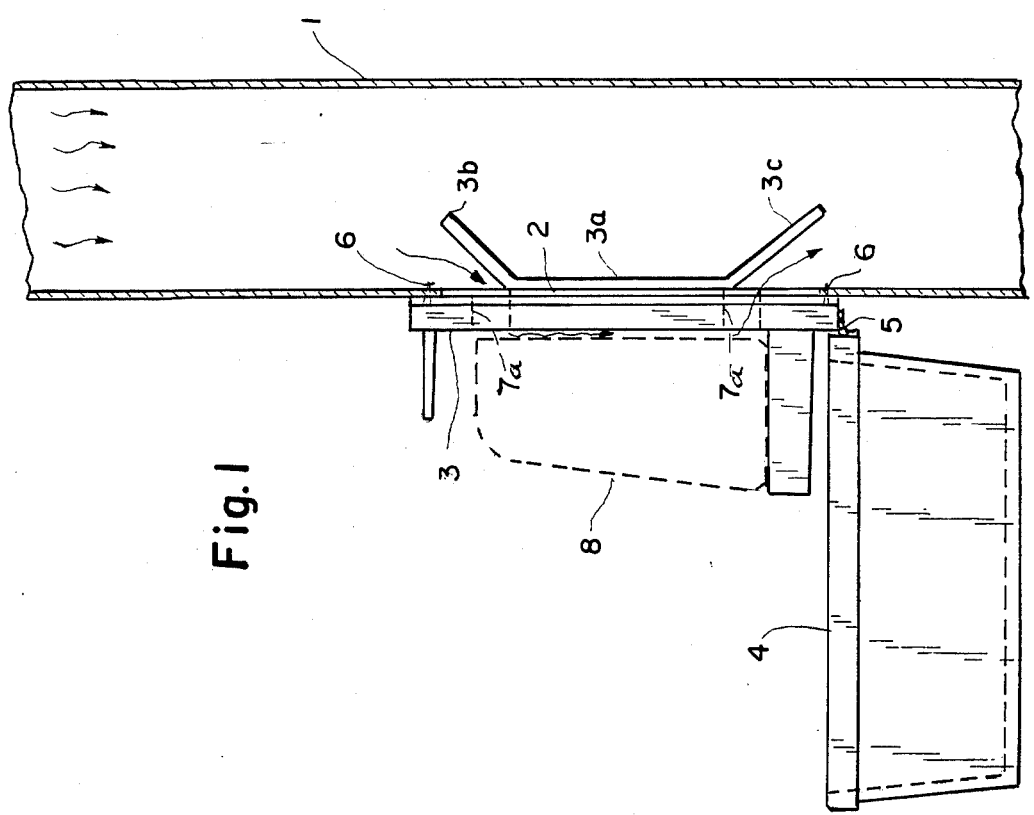

AIR FRESHENER

This invention relates to a forced air furnace air freshener.

BACKGROUND OF THE INVENTION

Disadvantages of present fresheners associated with a forced air furnace is that many are applied to grilles in individual rooms, as distinguished from scenting the entire home as done by the present invention. Moreover, they do not have long lives, nor are they easily replaceable or simple in construction as the present invention.

SUMMARY OF THE INVENTION

An object of the present invention is to provide an air freshener which overcomes the above-named disadvantages and, more particularly, an air freshener which can be mounted on a cold air return of a forced air furnace so as to enable scenting of the entire home. The air freshener of the present invention is essentially in the form of a basket enclosing a block of freshener and so mounted on the outside of a cold air return, that cold air therein will flow through the freshener by being diverted exteriorly of the duct to the block while enclosed in the closed basket. Easy access to enable replacement of the block of freshener is provided by merely opening the basket.

BRIEF DESCRIPTION OF THE DRAWING

FIG. 1 is a side view of the air freshener of the present invention, shown mounted on a cold air return illustrated in vertical cross-section;

FIG. 2 is an elevational view of the adjoining inside surface of the cold air return; and FIG. 3 is an elevational view of a modification of the scent mounting.

DESCRIPTION OF THE PREFERRED EMBODIMENTS

Referring more particularly to FIGS. 1 and 2, numeral 1 denotes a forced air furnace cold air return duct with cold air flowing in the direction of the arrows and having two openings 7,7 registering with holes 7a,7a formed in the lid 3 of the basket 4, hinged thereto by hinge 5. A gasket 2 is provided between the lid and furnace duct 1. The wall of the cold air return 1 is provided with holes 6a to enable fastening means 6 to support the lid 3 on the other wall surface of the cold air return. Holes 7,7 are provided in the duct 1 to enable cold air to be bypassed through them as shown by arrows and through a block 8 of scent mounted on the inside of lid 3, the flow being aided by flanges 3b and 3c of deflector 3a mounted on the inside wall of duct 1 which deflects cold air into one opening 7 and to the other opening 7, as indicated by the arrows.

In operation, the basket 4 is moved against its lid 3 to the closed position, enclosing scent block 8, so that during the flow of air in duct 1, it will be freshened or scented by block 8, of any scent, such as cherry, vanilla, pine, wintergreen, etc.

When it is desired to replace scent block 8, the basket is opened to the position shown in FIG. 1 to provide access thereto.

FIG. 3 shows a modification of the scent holder mounted on the inside of lid 3 comprising a wire or plastic spherical cage comprising halves 9, hinged at 10, and closed with clasp 11, for enclosing the scent and a ring or string 12 for supporting the cage. The advantage of this construction is to enable the partially used-up scent block to be supported in a room or in a car until completely depleted.

Thus it will be seen that I have provided an efficient air freshener which can be scented with any type of scent and which provides a constant intensity of scent throughout its life, also, which is applicable to other structures rather than homes, such as office buildings, hospitals, convalesent homes, movie theatres, night clubs, etc.

While I have illustrated and described several embodiments of my invention, it will be understood that these are by way of illustration only and that various changes and modifications may be contemplated in my invention and within the scope of the following claims.

I claim:

1. In combination with a cold air return duct of a forced air furnace, having a pair of vertically spaced openings in one wall thereof, a basket having a lid, said lid being mounted on the outside of said duct, said lid having holes in registry with said openings and which lid carries a scent block, a gasket between said lid and said outside of said duct, said basket being hinged to said lid and, when in the closed position of the basket, being adapted to completely enclose said scent block during normal operation of said air furnace, and deflector fins mounted on the inside wall of said duct immediately adjacent to said vertically spaced openings to deflect cold air return into said basket so as to enable cold air in said duct to be by-passed externally of the cold air return and through said scented block.

2. The combination recited in claim 1 wherein said scent block is supported in a foraminous container suspended on said lid for use elsewhere when the scent is partially depleted.

* * * * *